(12) United States Patent
Forsberg et al.

(10) Patent No.: US 8,236,303 B2
(45) Date of Patent: *Aug. 7, 2012

(54) USE OF β-1,3 (4)-ENDOGLUCANOHYDROLASE, β-1,3 (4) GLUCAN, DIATOMACEOUS EARTH, MINERAL CLAY AND GLUCOMANNAN TO AUGMENT IMMUNE FUNCTION

(75) Inventors: Neil E. Forsberg, Corvallis, OR (US); Steven B. Puntenney, Independence, OR (US)

(73) Assignee: OmniGen Research, LLC, Corvallis, OR (US)

( * ) Notice: Subject to any disclaimer, the term of this patent is extended or adjusted under 35 U.S.C. 154(b) by 520 days.

This patent is subject to a terminal disclaimer.

(21) Appl. No.: 11/668,375

(22) Filed: Jan. 29, 2007

(65) Prior Publication Data
US 2007/0202092 A1    Aug. 30, 2007

Related U.S. Application Data

(62) Division of application No. 10/829,633, filed on Apr. 5, 2004, now abandoned.

(51) Int. Cl.
*A61K 38/47*    (2006.01)

(52) U.S. Cl. ............ 424/94.61; 514/54; 426/2; 426/656

(58) Field of Classification Search ............... 424/94.51; 514/54; 426/2, 656, 807
See application file for complete search history.

(56) References Cited

U.S. PATENT DOCUMENTS

| | | | |
|---|---|---|---|
| 3,943,250 A | 3/1976 | Richter et al. | |
| 3,961,080 A | 6/1976 | Sugimoto et al. | |
| 4,055,667 A | 10/1977 | Linton et al. | |
| 4,138,479 A * | 2/1979 | Truscheit et al. | 424/278.1 |
| 4,251,519 A | 2/1981 | Robbins et al. | |
| 4,501,634 A | 2/1985 | Yoshimura et al. | |
| 4,619,859 A | 10/1986 | Yoshimura | |
| 4,714,716 A | 12/1987 | Park | |
| 4,729,902 A | 3/1988 | Urman et al. | |
| 4,765,992 A | 8/1988 | Geneix et al. | |
| 4,835,218 A | 5/1989 | Yoshimura et al. | |
| 4,857,512 A | 8/1989 | Wagner et al. | |
| 4,916,198 A | 4/1990 | Scheve et al. | |
| 5,032,401 A * | 7/1991 | Jamas et al. | 424/426 |
| 5,100,721 A | 3/1992 | Akao | |
| 5,149,549 A | 9/1992 | Beggs | |
| 5,165,946 A | 11/1992 | Taylor et al. | |
| 5,183,667 A | 2/1993 | Koch | |
| 5,192,547 A | 3/1993 | Taylor | |
| 5,272,236 A | 12/1993 | Lai et al. | |
| 5,278,272 A | 1/1994 | Lai et al. | |
| 5,346,963 A | 9/1994 | Hughes et al. | |
| 5,407,751 A | 4/1995 | Genske et al. | |
| 5,519,009 A | 5/1996 | Donzis | |
| 5,527,573 A | 6/1996 | Park et al. | |
| 5,639,492 A | 6/1997 | Turk et al. | |
| 5,698,599 A | 12/1997 | Subbiah | |
| 5,814,346 A | 9/1998 | Gamberini | |
| 5,871,966 A | 2/1999 | Kofod et al. | |
| 5,922,373 A | 7/1999 | Johnston | |
| 5,935,623 A | 8/1999 | Alonso-Debolt | |
| 6,045,834 A | 4/2000 | Howes et al. | |
| 6,221,381 B1 | 4/2001 | Shelford et al. | |
| 6,344,221 B1 | 2/2002 | Evans | |
| 6,395,311 B2 | 5/2002 | Jia | |
| 6,444,448 B1 * | 9/2002 | Wheatcroft et al. | 435/101 |
| 6,476,003 B1 | 11/2002 | Jordan et al. | |
| 6,541,678 B2 | 4/2003 | Klein | |
| 6,573,245 B1 | 6/2003 | Marciani | |
| 6,623,866 B2 | 9/2003 | Migliorini et al. | |
| 6,660,722 B2 | 12/2003 | Yvin et al. | |
| 7,939,066 B2 * | 5/2011 | Puntenney et al. | 424/94.61 |
| 2002/0048573 A1 | 4/2002 | Klock et al. | |
| 2004/0259015 A1 | 12/2004 | Tsubuko et al. | |
| 2005/0180964 A1 | 8/2005 | Puntenney et al. | |
| 2005/0220846 A1 | 10/2005 | Puntenney et al. | |
| 2007/0202092 A1 | 8/2007 | Puntenney et al. | |
| 2007/0253983 A1 | 11/2007 | Forsberg et al. | |

FOREIGN PATENT DOCUMENTS

| | | |
|---|---|---|
| DE | 4122906 A1 | 2/1992 |
| EP | 0551331 B1 | 11/1995 |
| EP | 0721741 A1 | 7/1996 |
| EP | 879844 A1 | 7/1996 |
| EP | 721006 A1 | 11/1998 |
| JP | 07184595 A | 7/1995 |
| WO | WO 95/30022 A1 | 11/1995 |
| WO | WO 97/02356 A1 | 1/1997 |
| WO | WO0044845 A1 | 8/2000 |

OTHER PUBLICATIONS

Pavelic, K et al. Immunostimulatory effect of natural clinoptilotie as a possible mechanism of its antimetastic ability. J Cancer Res Clin Oncol. 2002. 128: 37-44.*

Alexopoulos, C J, Mims, C W, Blackwell, M. Introductory Mycology. 1996. John Wiley & Sons. New York, Chapter 3, pp. 61-85.

(Continued)

*Primary Examiner* — Allison Ford
*Assistant Examiner* — Susan E Fernandez
(74) *Attorney, Agent, or Firm* — Klarquist Sparkman, LLP

(57) ABSTRACT

A method for the augmentation of immune function is described. The invention comprises a combination of β-1,3 (4)-endoglucanohydrolase, β-1,3(4)glucan, diatomaceous earth, mineral clay and glucomannan, which is fed to or consumed by mammalian or avian species in amounts sufficient to augment immune function. The invention described may be admixed with feeds or foods, incorporated into pelleted feeds or foods or administered orally to mammalian and avian species.

33 Claims, 11 Drawing Sheets

OTHER PUBLICATIONS

AOAC. Official Methods of Analysis of AOAC International. 1997. 16th Edition. vol. 1, , Chapter 4, p. 4 (4.1.10). AOAC Official Method 942.05 Ash of Animal Feed.

Catalano L, Picardi M, Anzivino D, Insabato L, Notar D, Bruno R. 1997. Small bowel infarction by *Aspergillus*. Haematologica vol. 82 pp. 182-183.

Czop, J. K., and K. F. Austen. 1985. A beta-glucan inhibitable receptor on human monocytes: its identity with the phagocytic receptor for particulate activators of the alternative complement pathway. J. Immunol. vol. 134 pp. 2588-2593.

Fontaine T, el al. 2000. Molecular Organization of the Alkali-insoluble Fraction of *Aspergillus fumigatus* Cell Wall. J Biol Chem vol. 275 pp. 27594-27607.

Frosco et al. May 14-18, 1989. Abstract F88, 89th meeting of the American Society for Microbiology, New Orleans, La.

Jaeger E E, Carroll N M, Choudhury S, Dunlop A A, Towler H M, Matheson M M, Adamson P, Okhravi N, Lightman S. Aug. 2000. Rapid detection and identification of Candida, *Aspergillus*, and *Fusarium* species in ocular samples using nested PCR. J Clin Microbiol vol. 38(8), pp. 2902-2908.

Jensen H E, Schonheyder H, Basse A. 1991. Acute disseminated *Aspergillosis* in a cow with special reference to penetration and spread. J. Comp. Path. vol. 104, pp. 411-417.

Jensen H E, Aalbaek B, Basse A, Schonheyder H. 1992. The occurrence of fungi in bovine tissues in relation to portals of entry and environmental factors. J. Comp Path. vol. 107, pp. 127-140.

McCausland I P, Slee K J, Hirst F S. May 1987. Mycotic abortion in cattle.. Australian Veterinary Journal. vol. 64, No. 5, pp. 129-132.

Ohsawa H. Feb. 1991. Clinical and pathological analysis of deep mycosis.. Kansenshogaku Zasshi. vol. 65(2) pp. 200-208.

Prescott R J, Harris M, Banerjee S S. Sep. 1992. Fungal infections of the small and large intestine. J Clin Pathol. vol. 45(9) pp. 806-811.

Puntenney S B, Wang Y, Forsberg N E. Mycotic infections in livestock: recent insights and studies on etiology, diagnostics and prevention of hemorrhagic bowel syndrome.

Proceedings of the 18$^{th}$ Southwest Nutrition and Management Conference, Feb. 20-21, 2003, Phoenix Arizona.

Rhodes J C, Jensen H E, Nilius A M, Chitambar C R, Farmer S G, Washburn R G, Steele P E, Amlung T W. 1992. *Aspergillus* and *Aspergillosis*. Journal of Medical and Veterinary Mycology , vol. 30, Supplement 1, pp. 51-57.

Tomee J F, Kauffman H F. Putative virulence factors of *Aspergillus fumigatus*. Apr. 2000. Clin Exp Allergy vol. 30(4) pp. 476-484.

Xia, Y., V. Vtvika, J. Yan, M. Hanikov, T. N. Mayadas, G. D. Ross. 1999. The B-glucan-binding lectin site of mouse CR3 (CD11b/CD18) and its function in generating a primed state of the receptor that mediates cytotoxic activation in response to iC3b-opsonized target cells. J. Immunol. vol. 162 pp. 2281.

Kessler, G. et al, Glucomannan-protein complexes from cell walls of yeast. 1959. Journal of Biological Chemistry. 234(9);2281-2285.

Magnoli, C et al. The mycoflora and toxicity of feedstuffs from a production plant in Cordoba, Argentina. 2002. Mycotoxin Research 18(1): 177-184.

Tangarone, B. et al. Purification and characterization of an endo-(1,3)-beta-D-glucanase from *Trichoderma longibrachiatum*. 1989. Applied and Environmental Microbiology 55(1):177-184.

Derwent Publications Ltd., London, GB; XP002359382 & RU 2 115 421 C1 (Devichenskii V M) Jul. 20, 1998, abstract.

Derwent Publications Ltd., London, GB; XP002359383 & RU 2 093 162 C1 (AS SIBE Biochem Int) Oct. 20, 1997, abstract.

International Search Report. PCT/US2005/02829. Jan. 16, 2006. pp. 1-4.

Opinion PCT/US2005/02829. Jan. 16, 2006. pp. 1-5.

Proposed Pretrial Order, *Alltech, Inc.* v. *Cenzone Tech, Inc*., U. S. District Court for the Southern District of California, Civil Action No. 06-CV-0153 JM (RBBx), Jul. 31, 2007.

Civil Docket for Case #: 3:06-cv-00153-JM-RBB, *Alltech, Inc.* v. *Cenzone Tech, Inc*., U.S. District Court, Southern District of California (San Diego).

Information Disclosure Statement, Jun. 18, 2007, filed in reexamination of Patent No. 6,045,834 (Reexamination Control No. 90/008,406).

Information Disclosure Statement, Aug. 16, 2007, filed in reexamination of Patent No. 6,045,834 (Reexamination Control No. 90/008,406).

Information Disclosure Statement, Oct. 29, 2007, filed in reexamination of Patent No. 6,045,834 (Reexamination Control No. 90/008,406).

T.P. Lyons, 1995, Biotechnology in the Feed Industry, Proceedings of Alltech's Eleventh Annual Syposium, Edited by TP Lyons and KA Jacques, Nottingham University Press pp. 1-29.

H.L. Trenholm, L.L. Charmley and D.B. Prelusky, 1996, Mycotoxin Binding Agents:An Update on What We Know, Proceedings of Alltech's Twelfth Annual Symposium, Eds. TP Lyons and KA Jacques, Nottingham, pp. 327-349.

L.L. Charmley, H.L. Trenholm and D.B. Prelusky, 1995 Mycotoxins: Their Origin, Impact and Importance . . . , Proceedings of Alltech's Eleventh Annual Symposium, Edited by TP Lyon and KA Jacques, Nottingham University Press pp. 41-63.

T.F. Savage and E.I. Zakrzewska, 1996, The Performance of Male Turkeys Fed A Starter Diet . . . , Proceedings of Alltech's Twelfth Annual Sumposium, Edited by TP Lyons and KA Jacques, Nottingham University Press, pp. 47-54.

H.L. Trenholm, L.L. Charmely, and D.B. Prelusky, Jan. 1997, Mycotoxin Binding Agents: An Update on What We Know, Zootecnica International, pp. 40-42.

H.J. Peppler, 1979, Production of Yeasts and Yeast Products, Microbial Technology, Microbial Processes vol. 1, 2$^{nd}$ Ed., Academic Press, pp. 157-185.

Product Bulletin, 2000, Bill W. Perkins, Biotech Development Company, Inc., Dexter, Missouri, T-Bind pp. 1-18.

Label, circa 2000, Cenzone Tech, Inc., Microbond.

Specification Sheet, Circa 2000, Cenzone Tech, Inc., A.I.P. Co., Ltd., Microbond, The proven microtoxin absorbent pp. 1-8.

Product Bulletin Cenzone Tech, Inc., Microbond, The Proven Micotoxin Adsorbent that Aids in The Binding and Diminishing the Adverse Effects of Mycotoxins, Dec. 9, 2005, pp. 8-14.

G. Devegowda, Paper presented at African Lecture Tour (10-15$^{th}$ Mar. 1997), Mycotoxins in Feed, Novel Biotechnological Solutions pp. 1-8.

Product Bulletin, circa 2000, Ciendax S.A. Pronady 500, 100% yeast cell wall (*Saccharomyces cerevisiae*), pp. 1-4.

B.K. Mahesh and G. Devegowda, Apr. 1996, Ability of Aflatoxin Binders to Bind Aflatoxin in Contaminated Poultry Feeds and Liquid Media in vitro, poster presented at Twelfth Symposium on Biotechnology in the Feed Industry.

U.S. Department of Health and Human Services Food and Drug Administration Center for Veterinary Medicine, Oct. 1999, Guidance for Industry, Dioxin in Anti-Caking Agent Used in Animal Feed and Feed Ingredients.

Information Disclosure Statement, Nov. 5, 2007, filed in reexamination of Patent No. 6,045,834 (Reexamination Control No. 90/008,406).

International Search Report and Opinion for PCT/US2007/066968 pp. 1-14 Oct. 8, 2007.

Patil et al, Aug. 2004, Immune response of calves to bentonite and alum adjuvanted combined vaccine . . . Indian Journal of Animal Sciences vol. 74 pp. 845-847.

Wang et al, Identification of the mechanisms by which Omnigen-AF, a nutritional supplement, augments immune function in ruminant livestock. 2004. Proceedings, Western Section, American Society of Animal Science. vol. 55, pp. 349-352.

Chapman et al, Effects of Omnigen AF on milk production and on lactation persistence in a commercial dairy setting, Jul. 2005, Journal od Animal Science vol. 83 (Suppl 1) Abstract T177.

Omnigen AF Product Information at www.omnigenresearch.com/feed.php.

Adrie et al., "Successful Cardiopulmonary Resuscitation After Cardiac Arrest as a Sepsis-Like Syndrome," *Circulation*, 106:562-568 (2002).

Burton et al., "Immunity and Mastitis. Some New Ideas for an Old Disease," *Vet Clin Food Anim*, 19:1-45, 2003.

Kougias et al., "Normal Human Fibroblasts Express Pattern Recognition Receptors for Fungal (1→3)-β-D-Glucans," *Infect. Immun.*, 69(6):3933-3938 (Jun. 2001).

Lowry et al., "Purified β-Glucan as an Abiotic Feed Additive Up-Regulates the Innate Immune Response in Immature Chickens Against *Salmonella enterica* Serovar *Enteritidis*," *International Journal of Feed Microbiology 98*, 93(3):309-318 (2005).

Travis, J., "Biologists Reveal the Proteins that First See Dangerous Microbes," *Science News*, 160(10):5pp. (Sep. 8, 2001).

Vetvicka, V., "β3-Glucans as Immunomodulators," *JANA*, 3(4):31-34 (2001).

Weber et al., "Pre-Translational Regulation of Neutrophil L-selectin in Glucocorticoid-Challenged Cattle," *Vet. Immunol. Immunopath.*, 83:213-240 (2001).

Werling et al., "Differential Production of Cytokines, Reactive Oxygen and Nitrogen by Bovine Macrophages and Dendritic Cells Stimulated with Toll-like Receptor Agonists," *Immunology*, 111:41-52 (2004).

White et al., "Haplotype Variation in Bovine Toll-like Receptor 4 and Computational Prediction of a Positively Selected Ligand-Binding Domain," *PNAS*, 100(18):10364-10369 (Sep. 2, 2003).

"TLR-1: Toll-like Receptor 1," http://web.archive.org/web/20041210144234/http://www.invivogen.com/genedescription/..., 2pp. (visited Aug. 10, 2010).

Office action, Canadian Application No. 2,619,219, filed Aug. 10, 2005, 3pp. (Nov. 1, 2011).

\* cited by examiner

PRIOR ART

PRIOR ART

PRIOR ART

USE OF β-1,3 (4)-ENDOGLUCANOHYDROLASE, β-1,3 (4) GLUCAN, DIATOMACEOUS EARTH, MINERAL CLAY AND GLUCOMANNAN TO AUGMENT IMMUNE FUNCTION

REFERENCE TO RELATED APPLICATION

This application is a divisional of application Ser. No. 10/829,633 filed Apr. 5, 2004 now abandoned and also claims priority from application Ser. No. 10/388,525 filed Mar. 17, 2003 which claims priority from 60/414,838, filed Sep. 27, 2002, each of which is incorporated by reference herein.

FIELD OF THE INVENTION

This disclosure relates to methods and compositions for the augmentation of immune function in mammalian and avian species.

BACKGROUND OF THE INVENTION

The immune system consists of two general features. These are: 1) the innate immune system and 2) the adaptive (antibody-mediated) immune system. The innate system represents the first line of defense against an invading pathogen (whether bacterial or fungal) and provides the adaptive immune system with enough time (3-5 days) for it to build up antibodies which are used to "fight" pathogens. While the innate and adaptive systems are often described separately, they function in tandem; striving to sequester and neutralize a pathogen challenge.

The innate immune system. The innate immune system consists of several interesting components: Aspects include:

1. Physical and chemical barriers to pathogens provided by epithelium, gastric acid and digestive enzymes.
2. Cells which engulf and digest invading pathogens (e.g., neutrophils).
3. Receptors on the surface of these cells which recognize and bind to pathogens.
4. Signaling molecules (e.g., chemokines, cytokines) which communicate sites of infection and regulate expression of immune genes.

Neutrophils. Neutrophils are among the most important cells of the innate immune system. They are the first cell to arrive at a site of infection. In mammals, there are billions of neutrophils of which about one-half are freely circulating in the blood (Burton and Erskine, 2003). The remainder are held in reserve in bone marrow where they are formed. Neutrophils express an extracellular binding protein on their membranes termed "L-selectin" (also termed CD62L). The role of L-selectin is to interact weakly with the endothelial cell wall thereby allowing the neutrophil to "roll" along the wall of a blood vessel and to "monitor" the cell wall for the presence of signals which indicate a local infection (FIG. 1). The presence of pathogens in peripheral tissues causes release of local chemicals which then signal a rolling neutrophil of an infection. In response to these signals, L-selectin is shed from the surface of the neutrophil (see FIG. 1) and other more adhesive molecules are expressed on its surface. These molecules essentially "glue" the neutrophil within the blood vessel adjacent to the site of infection. The activated neutrophil then migrates through the endothelial cell wall toward the invading pathogen. Interleukin-1β is produced by the neutrophil as a pro-inflammatory cytokine. This aids in mediating inflammation and in facilitating containment of invading pathogens. During neutrophil migration, chemical signals originating from the site of infection (such as TNF-β and interferon γ) activate the neutrophil to become a mature "killer cell". The mature neutrophil migrates toward the site of infection where it interacts with pathogen-associated microbial patterns (PAMPs) on the surface of pathogens via several types of receptors. These receptors are expressed on the surface of the neutrophil and include the following well-identified types (FIG. 2):

a—CD18 and CD14
 b—Toll-like receptors (TLRs)
 c—C3b and C3bi (complement factors)
 d—Fc Binding of neutrophils to pathogens via receptors. Both CD14 and CD18 receptors bind with lipopolysaccharide (LPS), a common polysaccharide structure associated with membranes of gram-negative bacteria. In addition, neutrophils express toll-like receptors (TLRs) which recognize and bind to additional structures associated with pathogens. So far, ten different toll-like receptors have been identified in mammals (FIG. 2 and Table 1). TLRs play a critical role in early innate immunity to invading pathogens by sensing microorganisms. These evolutionarily conserved receptors recognize highly conserved structural motifs only expressed by microbial pathogens, called pathogen-associated microbial patterns (PAMPs: Invivogen, 2004). Stimulation of TLRs by PAMPs initiates a signaling cascade that involves a number of proteins, such as MyD88 and IRAK (FIG. 2). This signaling cascade leads to the activation of the transcription factor NF-kB which induces the secretion of cytokines that direct the adaptive (i.e., antibody-mediated) immune response. TLRs are predominantly expressed in tissues involved in immune function, such as spleen and peripheral blood leukocytes, as well as those exposed to the external environment such as lung and the gastrointestinal tract. Ten human and nine mouse TLRs have been characterized, seven of which have had their ligands identified. For examples, TLR2 is essential for the recognition of a variety of PAMPs, including bacterial lipoproteins, peptidoglycan, and lipotechoic acids. TLR3 is implicated in virus-derived double-stranded RNA. TLR4 is predominantly activated by lipopolysaccharide. TLR5 detects bacterial flagellin and TLR9 is required for response to unmethylated CpG DNA (Table 1). Recently, TLR7 and TLR8 were shown to recognize synthetic antiviral molecules. These receptors are essential elements in host defense against pathogens by activating the innate immunity (Invivogen, 2004).

Bovine TLRS. Relatively few studies on PAMPs have been completed with bovine cells. So far, bovine immune cells have been reported to contain TLR2 and TLR4 (Werling et al., 2004). Polymorphisms have been reported in bovine TLR4 which may determine susceptibility to bovine respiratory disease and Johne's disease (White et al., 2003).

C3b and C3bi are components of the complement cascade whereas the Fc receptor binds to the "constant region" of antibodies. Hence, pathogens which are coated with complement factors or antibody (i.e., pathogens which are opsonized) are also recognized by activated neutrophils and are subsequently phagocytosed. In other words, activated neutrophils possess several means by which they recognize pathogens (Table 1).

Phagocytosis and killing. The binding of neutrophils, (and other phagocytic cells) to cell-surface markers of pathogens via these receptors, then permits the phagocytic cell to engulf the invading pathogen and "kill" it (FIG. 3). Presently, two mechanisms for "killing" are known. These include: 1) an oxidative burst, where the phagocyte expresses reactive oxygen species which destroy the phagocytosed pathogen, and 2)

fusion of the engulfed pathogen with a lysosome-like structure to form a "phagosome". The phagosome is rich in digestive enzymes which mediate complete digestion of pathogens.

Common infections. Mammalian and avian species are continually challenged by pathogens in the gastrointestinal track and in the lung. These are important sites for resident neutrophils where minimize pathogen invasion. In addition, the mammary gland of mammals represents a site for pathogen challenge. In all infections, the innate immune system plays a key initial role in fighting-off the initial immune challenge. The innate system is essential to allow the adaptive (antibody-mediated) system to develop and mount a more-specific and directed immune response.

Cooperation between the innate and acquired immune system in ruminants. Antibodies which are specific to an invading pathogen leak into a site of infection to optimize clearance of a pathogen. Individuals with a high titer against a specific antigen are able to deliver these antibodies into the site of infection via a leaky endothelium (arising from an inflammatory response). Arrival of reactive antibodies (i.e., IgG.sub.2) in the alveolus coats (opsonizes) the pathogen and, as noted previously, allows neutrophil recognition of pathogens via Fc receptors (Table 1) and phagocytosis.

Stress and immune function. Stress reduces individuals' abilities to fight disease. The negative effects of stress on the immune system are mediate by the steroidal stress hormones (cortisol, hydrocortisone and corticosterone). Burton and co-workers at Michigan State University (Weber et al., 2001) have identified the mechanism by which stress brings about a reduction in immune function. Specifically, they have documented that glucocorticoids (i.e., cortisol) "spike" near parturition (FIG. 4) and reduce L-selectin expression in neutrophils (FIG. 5). This compromises one important aspect of an individual's first line-of-defense against pathogen challenge. Specifically, a stressed, immunosuppressed individual has reduced ability to monitor endothelial cell lining for sites of infection and to attack and to sequester pathogens. This may result in an infection (FIG. 6).

SUMMARY OF THE INVENTION

The object of the present invention is to provide a novel and previously unknown method for augmentation of the immune system in mammalian and avian species. The invention may be applied to, but not limited to, mammalian and avian species and will reduce susceptibility of an individual to both fungal and bacterial diseases.

A further object of this invention is to provide a method for augmentation of immune function and to thereby minimize or obviate morbidities and mortalities caused by, but not limited to, pathogenic fungi and bacteria with a preparation comprising a combination of $\beta$-1,3(4)-endoglucanohydrolase, $\beta$-glucan, diatomaceous earth, glucomannan, and mineral clay, such as aluminum silicate, montmorillonite clay, bentonite or zeolite.

Another object of the invention is to provide a composition comprising a combination of $\beta$-1,3(4)-endoglucanohydrolase, $\beta$-glucan, diatomaceous earth, mineral clay, and glucomannan, which additively augments immune function and thereby, reduces potential of pathogenic fungi and bacteria to cause morbidities and mortalities in mammalian and avian species.

Additional objects, advantages and novel features of the invention will be set forth, in part, in the description that follows and will, in part, become apparent to those skilled in the art upon examination of the following or may be learned with the practice of the invention. To achieve the foregoing and other objects, and in accordance with the purposes of the present invention as described herein, a novel method is described for the augmentation of immune function of mammalian and avian species. In particular, this invention increases expression of neutrophil L-selectin and interleukin-1$\beta$ and thereby minimizes or eliminates the colonization of the epithelial surfaces and underlying parenchymal tissues by pathogenic fungi and bacteria, reduces the populations of pathogenic organisms in blood and thereby minimizes or eliminates pathologies directly caused by and indirectly caused by this colonization. The invention comprises a mixture of $\beta$-1,3(4)-endoglucanohydrolase, $\beta$-glucan, diatomaceous earth, mineral clay, and glucomannan. The diatomaceous earth is standard commercial grade available from a variety of sources. The $\beta$-1,3(4)-endoglucanohydrolase is produced from submerged fermentation of a strain of Trichoderma longibrachiatum. The $\beta$-1,3(4)glucan and glucomannan are derived from a commercial product and are an extraction from any of a number of yeast organisms. The mineral clay product is a standard commercial grade (examples include, but are not limited to, montmorillonite clay, bentonite and zeolite). Extractions and productions of diatomaceous earth, yeast cell wall extract and mineral clay are well known in the art and commercially-available.

The compositions which are provided by the invention can be fed to any mammalian or avian species including, but not limited to, bovine, equine, ovine, caprine and avian species. When admixed with the feed or food or fed as a supplement, the invention augments immune function thereby reducing colonization by pathogens. The invention also minimizes or eliminates invasion of the blood compartment by pathogenic fungi and bacteria. The invention thereby minimizes or eliminates the manifestations of the pathologies typically associated with epithelial and systemic fungal and bacterial infections. Administration of the product may be used as a prophylactic (i.e., to prevent colonization and growth of pathogenic fungal and bacterial species in mammalian or avian species), as an additive to feeds or foods infected with pathogenic fungi or bacteria or as a preferred method to treat and thereby minimize or eliminate an existing, diagnosed or non-diagnosed, fungal or bacterial infection. Application of the invention as described herein and via the specific and novel mechanisms described herein will minimize and possibly eliminate manifestations of fungal and bacterial infections. Application of the invention as described herein will also minimize or possibly eliminate manifestations associated with the presence of pathogenic fungal and bacterial organisms, as identified above, in food or feed of mammalian and avian species.

BRIEF DESCRIPTION OF THE DRAWINGS

The accompanying drawings and photographs which are incorporated into the following "Detailed Description of the Invention" form part of the specification and illustrate several aspects of the present invention and, together with the Detailed Description, serve to explain the details of the invention. In the following section five figures are presented.

FIG. 7. Effect of five experimental treatments on concentrations of neutrophil L-selectin. An experiment was conducted with 60 sheep. Twelve sheep were allocated to each treatment. The treatments consisted of:

1. Control
2. Immunosuppressed (daily injections of Azium [Dexaméthasone], 0.1 mg/kg twice/day).
3. Immunosuppressed plus experimental product fed at 0.5% of daily dry matter intake.
4. Immunosuppressed plus moldy feed (addition of *Aspergillus fumigatus*-infected wheat mill run; 1.5 lbs/head/day).
5. Immunosuppressed plus moldy feed (as in Treatment 4) plus the experimental feed product as outlined in Treatment 3.

The duration of the trial was 28-days. On Day 28, blood was taken from six sheep per treatment and neutrophils were recovered by Percoll gradient centrifugation. The concentrations of L-selectin were determined by Western blot analysis using an antibody specific to L-selectin. Relative concentrations of L-selectin among the five treatment groups are shown in FIG. 8.

Figure 1:
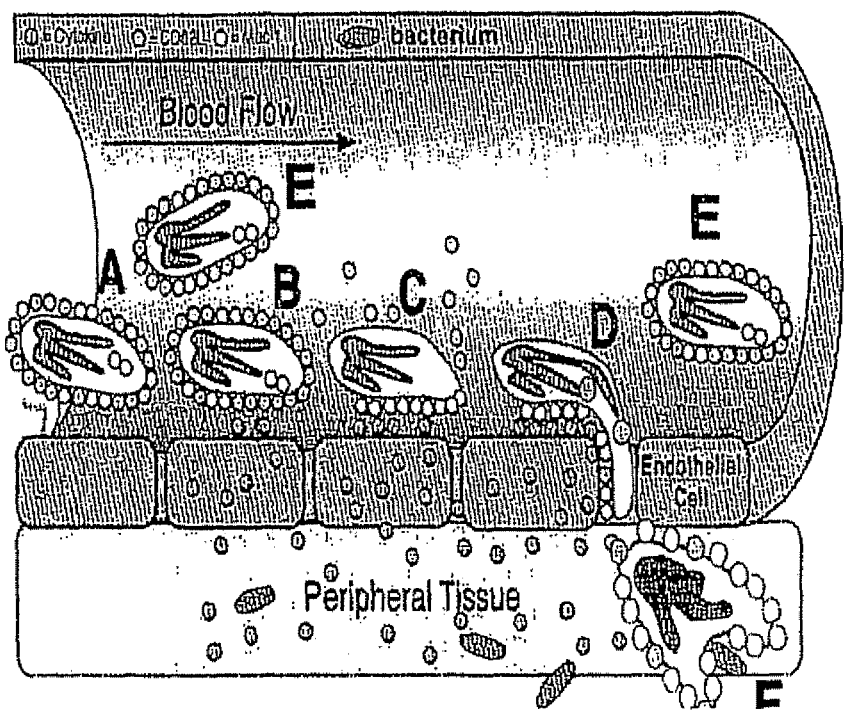
FIG. 1 is a schematic drawing illustrating the movement of neutrophils through a blood vessel, L-selectin (CD62L) is shown as circles on the surface of the neutrophils A-E. These allow docking of the neutrophils with endothelium. There is shedding of L-selecting and migration of neutrophil into peripheral tissue toward a site of infection F. (Source: Burton and Erskine, 2003.)
Figure 2:
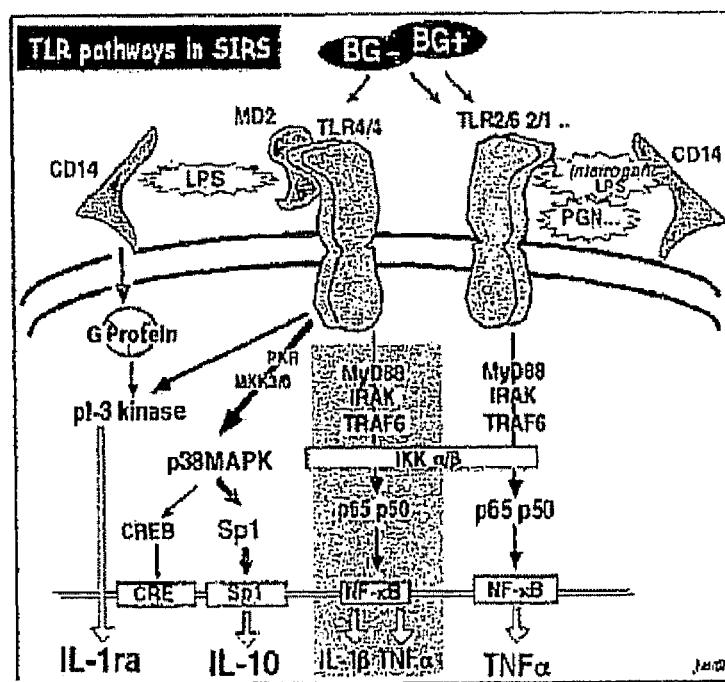
FIG. 2 is a schematic diagram illustrating toll-like receptors (TLRs) on the surface of an immune cell, and signal transduction following binding of TLRs with microbial PAMPs (pathogen-associated molecular patterns). (Source: M. Adib-Conquy, C. Fitting, 2002.)
Figure 3:
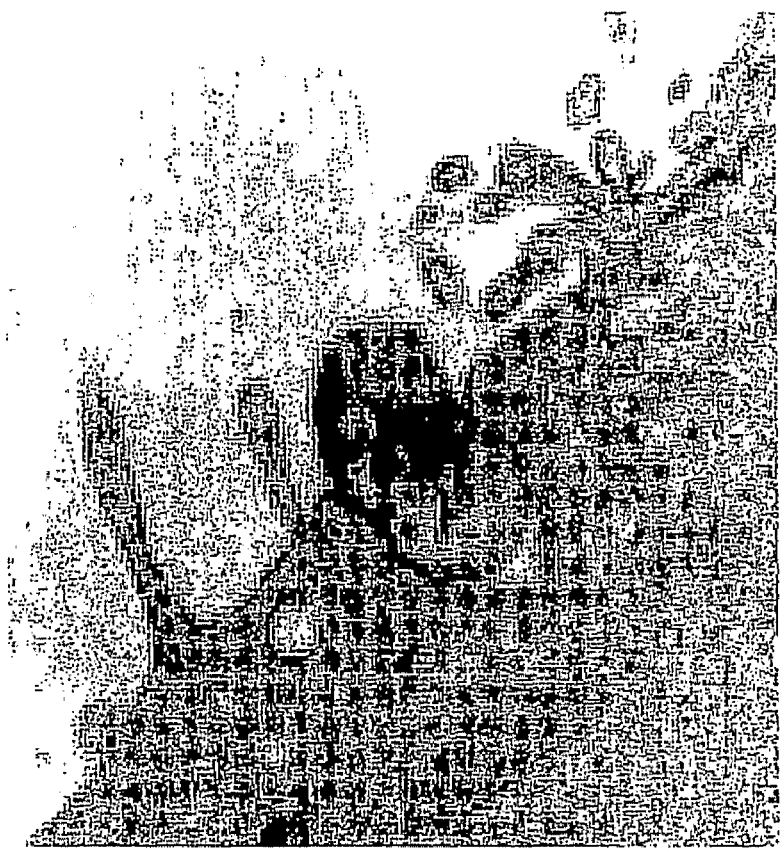
FIG. 3 illustrates a macrophage cell engulfing a bacterium in a process called phagocytosis. Toll-like and other receptor direct phagocytes to recognize microbes. Pseudopodial projections surround the bacterium. (Source: Travis, 2002.)
Figure 4:
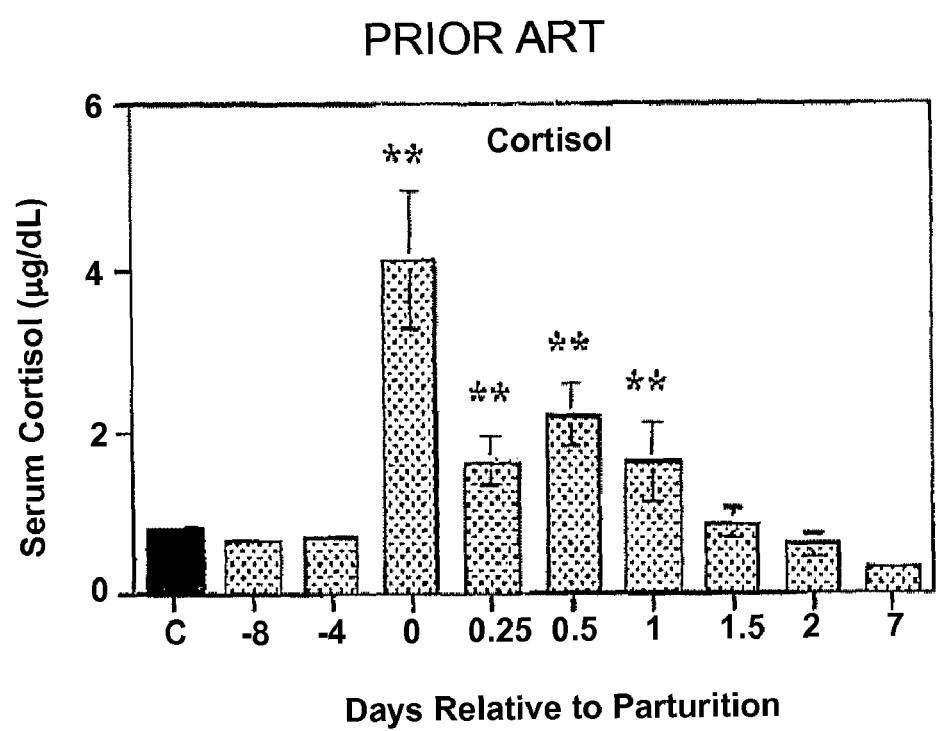
FIG. 4 is a bar graph of cortisol levels in dairy cattle relative to day of parturition. Cortisol peaks at day of parturition. (Source: Weber et al., 2001.)
Figure 5:
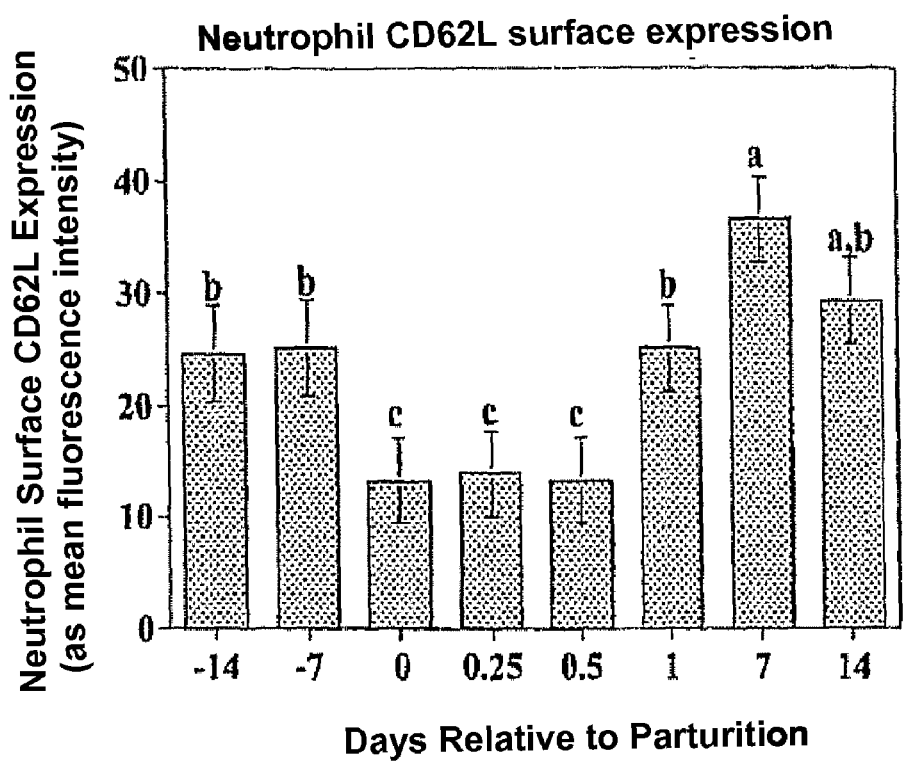
FIG. 5 is a bar graph of neutrophil surface CD62L (L-selectin) expression in cattle relative to day of parturition. (Source: Weber et al, 2001.)
Figure 6:
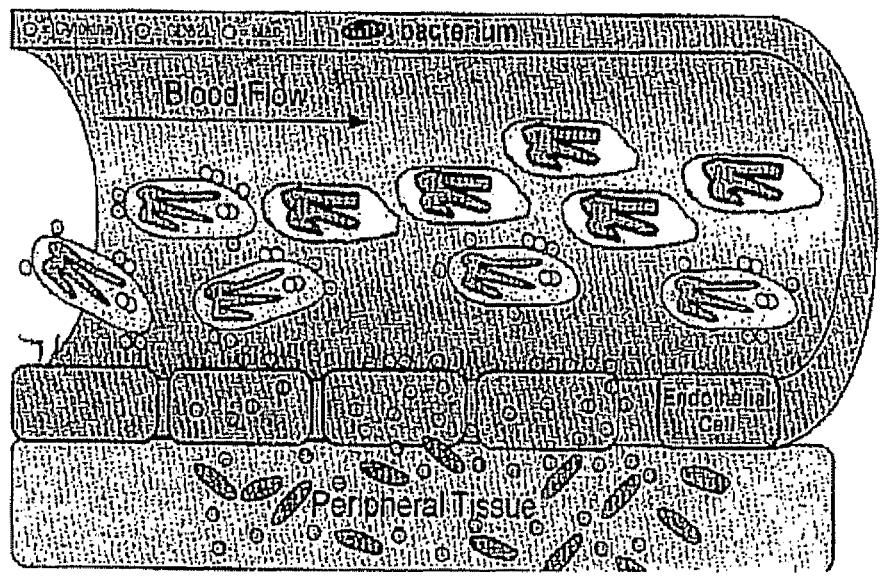
FIG. 6 is a schematic diagram illustrating neutrophils lacking L-selectin expression in a stressed dairy cow. (Source: Burton and Erskine, 2003.)
Figure 7:
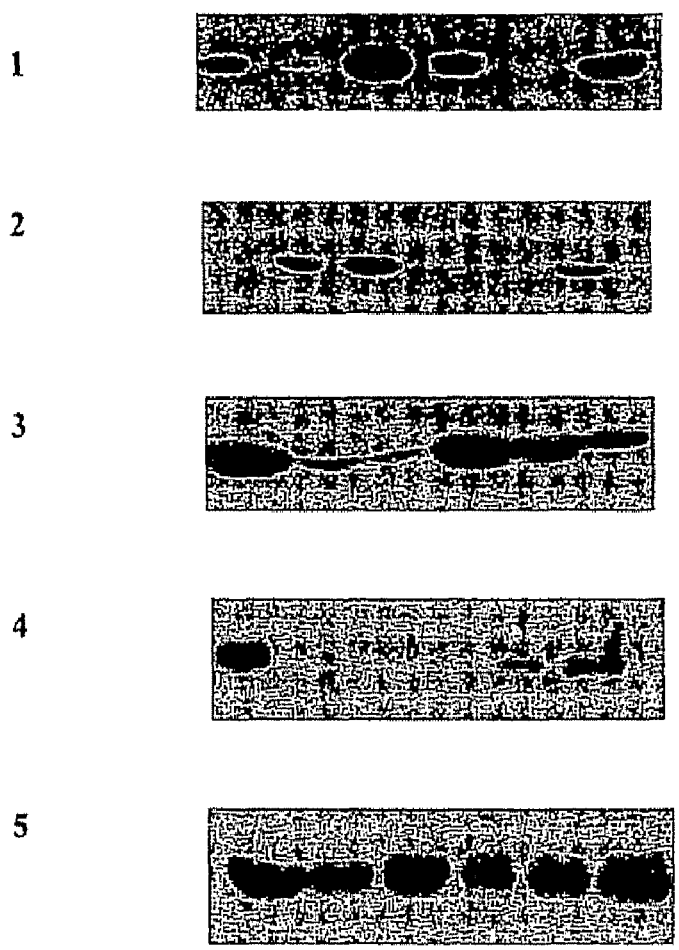
Figure 8:
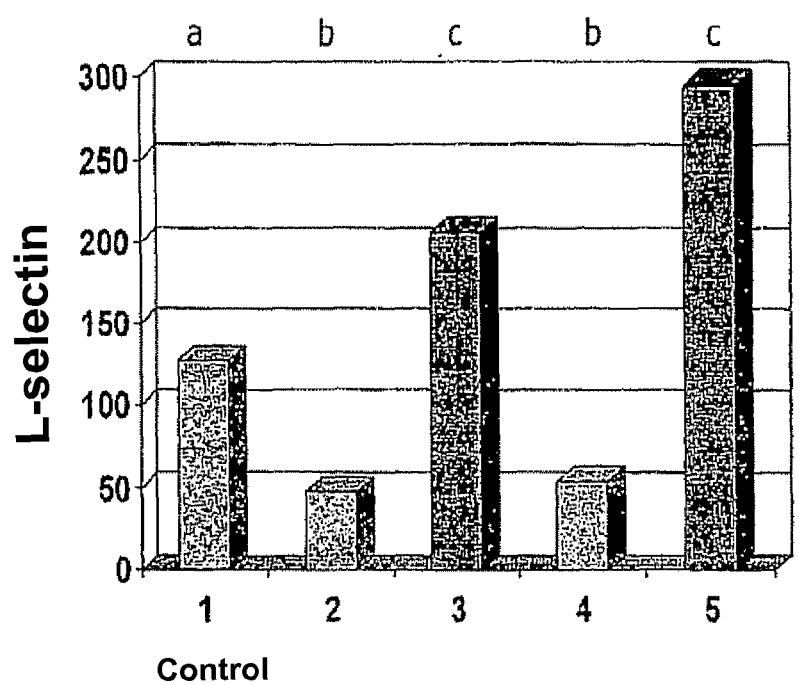

FIG. 8. Scanning densitometry of data shown in FIG. 7.

Figure 9:
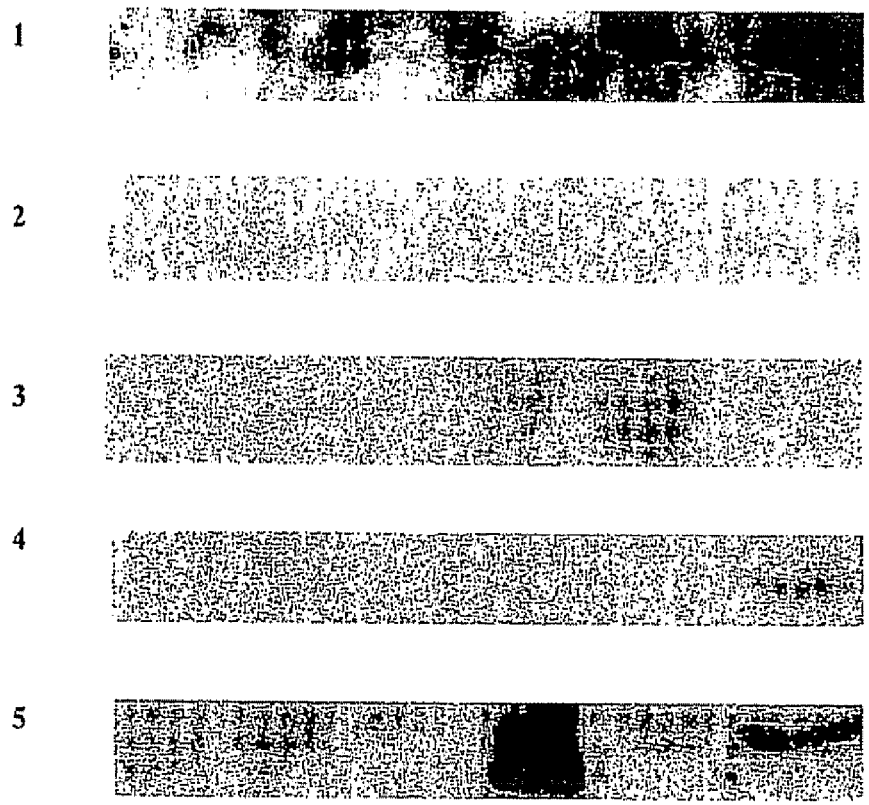

FIG. 9. Analysis of neutrophil interleukin-1β in the same sheep neutrophil samples presented in FIG. 7.

Figure 10:
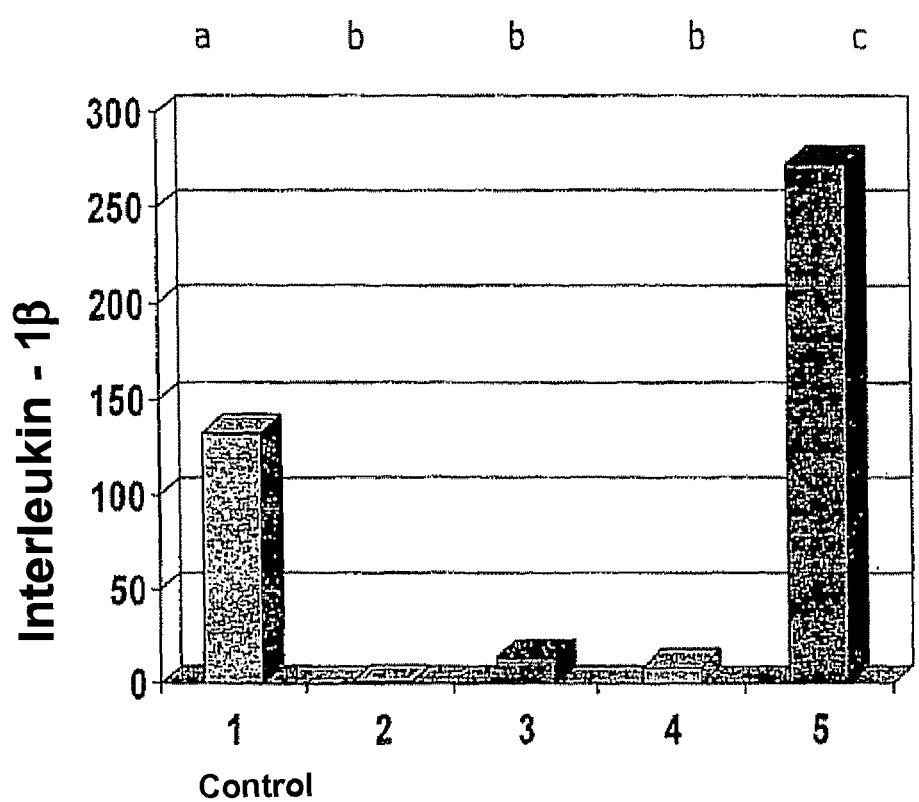

FIG. 10. Scanning densitometry of data shown in FIG. 9.

Figure 11:
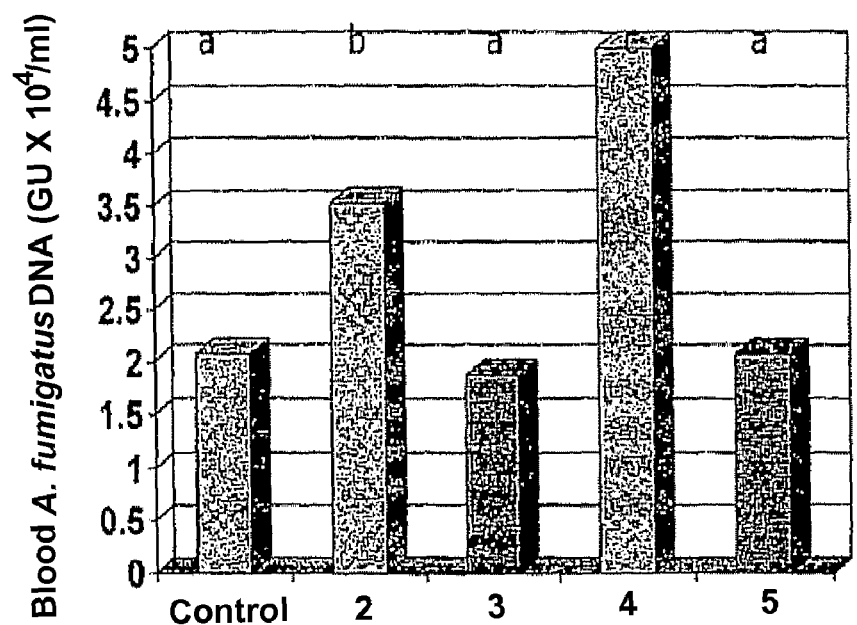

FIG. 11. Concentrations of *Aspergillus fumigatus* in blood samples taken from sheep on Day 28 of the above study. *A. fumigatus* DNA levels were assessed using a quantitative Sybr-Green PCR-based assay specific for *A. fumigatus*.

DETAILED DESCRIPTION OF THE INVENTION

The present invention is based on the novel discovery that a combination of β-1,3(4)-endoglucanohydrolase, β-1,3(4) glucan, diatomaceous earth, mineral clay, and glucomannan effectively augments immune function and reduces colonization of tissues and blood by a pathogen.

The β-1,3(4)-endoglucanohydrolase is from a commercial source and is produced from submerged fermentation of a strain of *Trichoderma longibrachiatum*.

The diatomaceous earth is prepared by methods commonly known in the art. It is available as a commercially-available acid-washed, product with 95% silica ($SiO_2$) and with its remaining components not assayed but consisting primarily of ash (minerals) as defined by the Association of Analytical Chemists (AOAC, 2002).

The yeast cell wall extract is prepared by a method commonly known in the art. It is a commercial source of β-1,3(4) glucan and glucomannan derived from primary inactivated yeast (Saccharomyces cerevisiae) with the following chemical composition:

| Moisture | 2-3% |
| --- | --- |
| Dry matter | 97-98% |
| Proteins | 14-17% |
| Fats | 20-22% |
| Phosphorous | 1-2% |
| Mannans | 22-24% |
| β-1,3-(4)glucan | 24-26% |
| Ash | 3-5% |

The mineral clays (aluminosilicates) used in this invention may be fulfilled by any of a variety of commercially-available clays including, but not limited to, montmorillonite clay, bentonite and zeolite.

In a preferred embodiment of the invention, β-1,3(4)-endoglucanohydrolase, diatomaceous earth, yeast cell wall extract and mineral clay are combined at 0.05-3%, 1-40%, 1-20% and 40-92%, respectively. In a preferred composition, β-1,3(4)-endoglucanohydrolase, diatomaceous earth, yeast cell wall extract and mineral clay are combined at 0.1-3%, 5-40%, 2-10% and 40-80%, respectively. In an especially preferred embodiment of the invention, β-1,3(4)-endoglucanohydrolase, diatomaceous earth, yeast cell wall extract and mineral clay are combined at 0.2-3%, 30-40%, 4-6% and 50-65%, respectively. The preferred physical form of the invention is a dry, free-flowing powder which is suitable for direct inclusion into a feed, food product or as a supplement to a total mixed ration or diet.

The compositions provided by the present invention may be incorporated directly into commercially-available feeds or food products or fed as supplements to commercially-available feeds or food products. The composition contained in the present invention may be fed to any mammalian or avian species. The methods of the invention comprise augmenting immune function in mammalian and avian species. When incorporated directly into feeds, the present invention may be added to feeds in amounts ranging from 0.1 to 5 kg per ton of feed. In an especially preferred composition, the invention may be added to feeds in amounts ranging from 1-2 kg per ton of feed.

The composition contained in the present invention may be added to animal feedstuffs or to foods in amounts ranging from 0.0125% to 2% by weight of feed. In a preferred embodiment, the composition is added to animal feedstuffs or to food in amounts from 0.0625% to 1% by weight of feed. In an especially preferred embodiment, the invention is added in amounts from 0.125% to 0.5% by weight of feed.

Alternatively, the composition contained in the present invention may be fed directly to mammalian or avian species as a supplement in amounts 0.016 grams/kg to 0.37 grams/kg of live body weight per day. In an especially preferred embodiment, the invention may be provided to mammalian and avian species in amounts of 0.10 grams/kg to 0.20 grams/kg of body weight per day. One of skill in the art can appreciate that the amount of the invention fed can vary depending upon the animal species, size of the animal and type of the feedstuff to which the invention is added.

The novel methods of this invention comprise the ability of a combination of β1,3(4)-endoglucanohydrolase, diatomaceous earth, yeast cell wall extract and clay to augment immune function. The benefits resulting from the application of the invention to mammalian species include, but are not limited to, reduced death losses, reduced incidence of mycotic abortion, reduced incidence of jejunal hemorrhage syndrome (dead gut syndrome), reduced incidence of scouring (diarrhea), improved growth rate, improved efficiency of growth, improved milk production, improved efficiency of milk production and reduced somatic cell counts in milk products (dairy animals). The benefits from the application of the invention to avian species include, but are not limited to, reduced death losses, improved growth and egg production, improved fertility, and reduced incidence of enteric diseases.

The following are intended to be illustrative of the invention, and are not to be considered restrictive of the scope of the invention as otherwise described herein.

EXAMPLE 1

An experiment was conducted using 60 growing male and female sheep. Sheep were allocated to one of the five treatments (seven females and five males per treatment):

1. Control.
2. Immunosuppressed (daily injections of Azium [Dexamethasone], 0.1 mg/kg twice/day).
3. Immunosuppressed plus the invention fed at 0.5% of daily dry matter intake.
4. Immunosuppressed plus moldy feed (addition of *Aspergillus fumigatus*-infected wheat mill run; 1.5 lbs/head/day).
5. Immunosuppressed plus moldy feed (as in Treatment 4) plus the invention as outlined in Treatment 3.

Animals were fed a dairy-type diet for a period of 28 days. Immunosuppression was mediated in Treatments 2, 3, 4 and 5 by daily injection of Azium using a high dose (a model of extreme stress: Weber et al., 2001). Sheep on Treatments 4 and 5 were challenged with a pathogenic mold by feeding wheat mill run which had been contaminated with a pathogenic mold (*Aspergillus fumigatus*). Sheep on Treatments 3 and 5 were supplemented with the invention at a rate of 0.5% of their daily dry matter intake. Following 28 days, blood samples were taken via jugular puncture and the neutrophil fractions were isolated using Percoll density gradient centrifugation. Following this, samples of neutrophil protein were processed using sodium dodecyl sulfate polyacrylamide gel electrophoresis and Western blotting using antibodies which are specific for L-selectin and interleukin-1-β. Relative concentrations of L-selectin and interleukin-1-β. were assessed using scanning densitometry.

FIGS. 7 and 8 demonstrate effects of the five experimental treatments on neutrophil L-selectin. Injection with Azium caused a marked reduction ($P<0.05$) in L-Selectin and provides evidence that Azium injection was, in fact, immunosuppressive. Addition of mold to the diets had no effect ($P>0.05$) on L-selectin concentrations. Of interest, addition of the invention to feed (Treatments 3 and 5) caused restoration (augmentation: $P<0.05$) of L-selectin.

Interpretation: The novel invention successfully restored (augmented) normal levels neutrophil L-selectin.

Restoration of L-selectin on neutrophil surfaces will re-establish their ability to monitor the endothelial lining for pathogens.

FIGS. 9 and 10 demonstrate effects of the five experimental treatments on neutrophil interleukin-1-β concentrations. Azium treatment caused a marked reduction ($P<0.05$) in neutrophil inerleukin-1-β concentration. This demonstrates that Azium was immunosuppressive. The novel invention had no effect ($P>0.05$) on neutrophil interleukin-1-β in the absence of a pathogen challenge (i.e., Treatment 3 versus Treatment 2); however the invention caused a marked increase ($P<0.05$) in neutrophil interleukin-1-β in the presence of a pathogen challenge (i.e., Treatment 5 versus Treatment 4).

Interpretation. Interleukin-1β is an important pro-inflammatory cytokine which enables the neutrophil to fulfill its role as a phagocyte. Ability of the feed product to restore interleukin-1β. in the presence of a pathogen (*A. fumigatus*) demonstrates that pathogens potential effects of the invention on immune function.

FIG. 11 shows the effects of the five experimental treatments on blood concentrations of *A. fumigatus*. *A. fumigatus* concentrations were determined using a Sybr-Green real-time quantitative polymerase chain reaction (PCR) assay developed in our laboratory. The results demonstrate that the invention reduced ($P<0.05$) *A. fumigatus* concentrations in blood.

Interpretation. The restoration of neutrophil function shown in FIGS. 7-10 manifests itself by reducing pathogen load detected within the blood compartment. The invention reduces pathogen load.

These results show that the composition of the invention (i.e., mineral clay, yeast cell wall extract, diatomaceous earth and β-1,3(4)-endoglucanohydrolase) is capable of a previously-undescribed effect of augmenting immune function. The invention specifically restores levels of L-selectin and interleukin-1-β in neutrophils thereby restoring the ability of neutrophils to monitor for the presence of invading pathogens.

The combination of products augments immunity in mammalian and domestic species and thereby prevents the invasion and colonization of the blood compartment. It represents a mixture which is flowable and easily incorporated into feed products and food products. The present invention was effective in achieving its immunostimulatory effects under growth conditions which might be found in mammalian and avian digestive systems where nutrients, moisture, oxygen and elevated temperatures are provided by the host.

The foregoing description of the preferred embodiment of the invention has been presented for purposes of illustration and description. It is not intended to be exhaustive or to limit the invention to the precise form disclosed. Obvious modifications or variations are possible in light of the above illustrations. The embodiment was chosen and described to provide the best illustration of the principles of the invention and its practical application to thereby enable one of ordinary skill in the art to utilize the invention in various embodiments and with modifications as are suited to the particular use contemplated. All such modifications and variations are within the scope of the invention as determined by the appended claims when interpreted in accordance with the breadth to which they are fairly, legally and equitably entitled.

TABLE 1

Summary of mechanisms by which neutrophils can recognize/bind to pathogen prior to phagocytosis.

| Neutrophil receptor | PAMP[1] or Ligand | Comment |
| --- | --- | --- |
| CD14 | lipopolysaccharide | direct binding to pathogen |
| CD18 | lipopolysaccharide | direct binding to pathogen |
| TLR2 | lipoprotein, peptidoglycan, lipotechoic acid | direct binding to pathogen |
| TLR3 | virus-derived double-stranded RNA | direct binding to pathogen |
| TLR4 | lipopolysaccharide | direct binding to pathogen |
| TLR5 | Flagellin | direct binding to pathogen |
| TLR7/8 | Small synthetic anti-viral molecules | direct binding to pathogen |

TABLE 1-continued

Summary of mechanisms by which neutrophils can recognize/bind to pathogen prior to phagocytosis.

| Neutrophil receptor | PAMP[1] or Ligand | Comment |
| --- | --- | --- |
| TLR 9 | unmethylated CpG DNA | direct binding to pathogen |
| C3b/C3bi | Complement factors | binds opsonized pathogen |
| Fc | "constant region" of antibodies | binds opsonized pathogen |

[1]PAMP: Pattern-associated molecular pattern

What is claimed is:

1. A method for augmenting function of an animal's innate immune system, comprising:
    providing a composition comprising a combination of β-glucans, β-1,3(4)-endoglucanohydrolase, diatomaceous earth, a mineral clay, and glucomannan; and
    administering said composition to an animal selected from mammalian and avian species and known to have been exposed to a pathogen, thereby augmenting the animal's innate immune function and reducing susceptibility to an infection.

2. The method of claim 1 comprising administering the composition to an immunosuppressed mammalian or avian species.

3. The method of claim 2 wherein said animal is immunosuppressed as result of a cause selected from the group consisting of pregnancy, elevated stress hormone levels, drug treatment and pathogen exposure and combinations thereof.

4. The method of claim 2, wherein the pathogen is a pathogenic mold.

5. The method of claim 4, further comprising feeding the animal moldy feed, wherein the moldy feed is the source of the pathogen.

6. The method of claim 1 wherein said augmenting of the function of the animal's innate immune system includes increasing the expression of a molecule selected from the group consisting of L-selectin and interleukin-1β and combinations thereof.

7. The method of claim 1 wherein said mammalian species include all ruminant animals.

8. The method of claim 1 wherein said mammalian species include dairy cattle, beef cattle and sheep.

9. The method of claim 1 wherein said mammalian species include sheep.

10. The method of claim 1 wherein said avian species include poultry species used in commercial livestock production.

11. The method of claim 1, wherein the mineral clay comprises montmorillonite, bentonite, aluminosilicate, or zeolite clays, or mixtures thereof.

12. The method of claim 1, wherein the β-1,3(4)-endoglucanohydrolase is produced from submerged fermentation of Trichoderma ongibrachiatum.

13. The method of claim 1, wherein the β-glucans and glucomannan are derived from boiling and enzyme autolysis of gram positive yeast cell walls from the genera of Saccharomyces.

14. The method of claim 13, wherein the β-glucans and glucomannan are derived from boiling and enzyme autolysis of gram positive yeast cell walls from Saccharomyces cerevisiae.

15. The method of claim 1, wherein said diatomaceous earth is calcined at a minimum temperature of 900° C.

16. The method of claim 1, wherein said composition comprises between 15% and 40% diatomaceous earth, between 50% and 81% mineral clay, between 1.0% and 5.0% β-glucans, between 0.05% and 3.0% β-1,3(4)-endoglucanohydrolase and between 1% and 8.0% glucomannan.

17. The method of claim 1, wherein said composition comprises between 20% and 30% diatomaceous earth, between 60% and 75% mineral clay, between 1.0% and 3.5% β-glucans, between 0.1% and 3.0% β-1,3(4)-endoglucanohydrolase and between 1.0% and 6.0% glucomannan.

18. The method of claim 1, wherein said composition is admixed into foods or animal feedstuffs in a concentration of between 0.0125% and 5% by weight for the purpose of inhibiting fungal growth in feed, food or digesta.

19. The method of claim 1, wherein said composition is admixed into a food or feedstuff and is subsequently fed to domestic livestock.

20. The method of claim 1, wherein said composition is admixed into a food or feedstuff and is subsequently fed to ruminant livestock or avian livestock.

21. The method of claim 1 wherein said composition is a prophylactic when administered to said animal.

22. The method of claim 1 wherein said composition is administered to said animal contemporaneously with the exposure to the pathogen.

23. The method of claim 1 wherein said administering of said composition increases neutrophil function.

24. The method of claim 1 wherein said administering of said composition reduces pathogen load in the blood.

25. The method of claim 1 wherein said administering of said composition increases the expression levels of neutrophil L-selectin in said animal.

26. The method of claim 1 wherein said administering of said composition increases the expression levels of interleukin-1β in said animal.

27. The method of claim 1 wherein said administering of said composition increases neutrophil phagocytosis in said animal.

28. The method of claim 1 wherein said administering of said composition increases oxidative burst killing in said animal.

29. The method of claim 1 wherein said administering of said composition increases extrusion of neutrophil extracellular traps in said animal.

30. The method of claim 1 wherein the providing comprises formulating the composition.

31. The method of claim 1 wherein the composition consists essentially of β-glucans, β-1,3(4)-endoglucanohydrolase, diatomaceous earth, a mineral clay, and glucomannan.

32. The method of claim 1, wherein the pathogen is a pathogenic mold.

33. The method of claim 1, further comprising exposing the animal to the pathogen.

* * * * *

UNITED STATES PATENT AND TRADEMARK OFFICE
CERTIFICATE OF CORRECTION

PATENT NO. : 8,236,303 B2  Page 1 of 1
APPLICATION NO. : 11/668375
DATED : August 7, 2012
INVENTOR(S) : Forsberg et al.

It is certified that error appears in the above-identified patent and that said Letters Patent is hereby corrected as shown below:

In the Claims:

Column 9, line 56, "*Trichoderma ongibrachiatum*" should be --*Trichoderma longibrachiatum*--

Signed and Sealed this
Nineteenth Day of April, 2016

Michelle K. Lee
*Director of the United States Patent and Trademark Office*